(12) United States Patent
Hall et al.

(10) Patent No.: US 11,107,558 B2
(45) Date of Patent: Aug. 31, 2021

(54) SYSTEM AND METHOD FOR GENERATING PATIENT TEST DATA PROCESSING CODE

(71) Applicant: Goodmark Medical (International) Limited, Lothian (GB)

(72) Inventors: Steven Hall, Edinburgh (GB); Michael Clarke, Edinburgh (GB)

(73) Assignee: Goodmark Medical (International) Limited, Edinburgh (GB)

(*) Notice: Subject to any disclaimer, the term of this patent is extended or adjusted under 35 U.S.C. 154(b) by 985 days.

(21) Appl. No.: 15/521,455

(22) PCT Filed: Oct. 19, 2015

(86) PCT No.: PCT/GB2015/053099
§ 371 (c)(1),
(2) Date: Apr. 24, 2017

(87) PCT Pub. No.: WO2016/063018
PCT Pub. Date: Apr. 28, 2016

(65) Prior Publication Data
US 2018/0277240 A1      Sep. 27, 2018

(30) Foreign Application Priority Data
Oct. 24, 2014   (GB) ................................. 1419021

(51) Int. Cl.
*G16H 10/40*        (2018.01)
*G16H 10/60*        (2018.01)
(Continued)

(52) U.S. Cl.
CPC ............. *G16H 10/40* (2018.01); *G16H 10/60* (2018.01); *G16H 40/63* (2018.01)

(58) Field of Classification Search
None
See application file for complete search history.

(56) References Cited

U.S. PATENT DOCUMENTS

2003/0216621 A1   11/2003   Alpert et al.
2005/0055242 A1*   3/2005   Bello ................. G06Q 50/22
                                                            705/2
(Continued)

FOREIGN PATENT DOCUMENTS

WO     WO 03/012635 A2    2/2003

OTHER PUBLICATIONS

"Testing medical embedded software", Havlice et al., IEEE, Jan. 23-25, 2014 (Year: 2014).*
(Continued)

*Primary Examiner* — Daxin Wu
(74) *Attorney, Agent, or Firm* — Blank Rome LLP

(57) ABSTRACT

A computer system for generating code for use in processing patient test data from point of care devices, the computer system comprises object definition storage storing a plurality of definition objects, each definition object defining a generic function to be performed in response to an output of a point of care device; instantiation data storage storing instantiation data for use in instantiating definition objects as processing objects for specific functions to be performed in response to outputs from specific point of care devices; and a code generating processor for generating code for at least one processing object to perform at least one specific processing function to process an output from a point of care device by accessing at least one definition object in the object definition storage and the instantiation data in the instantiation data storage to instantiate the at least one definition object using instantiation data for the point of care device.

6 Claims, 15 Drawing Sheets

(51) Int. Cl.
*G06F 8/30* (2018.01)
*G16H 40/63* (2018.01)

(56) References Cited

U.S. PATENT DOCUMENTS

| | | | |
|---|---|---|---|
| 2008/0134133 A1* | 6/2008 | DelloStritto | H04L 67/10 |
| | | | 717/101 |
| 2010/0154124 A1* | 6/2010 | Zerhusen | G16H 10/60 |
| | | | 5/658 |
| 2011/0153278 A1 | 6/2011 | Kurabayashi et al. | |
| 2013/0080832 A1 | 3/2013 | Dean et al. | |
| 2013/0325515 A1* | 12/2013 | Nikolova-Simons | |
| | | | G06Q 50/24 |
| | | | 705/3 |
| 2014/0089004 A1* | 3/2014 | Frey | G06Q 10/04 |
| | | | 705/3 |
| 2014/0114687 A1* | 4/2014 | Frank | G16H 20/30 |
| | | | 705/3 |
| 2014/0365830 A1* | 12/2014 | Rajan | G06F 11/3664 |
| | | | 714/38.1 |
| 2015/0051922 A1 | 2/2015 | Rentas et al. | |

OTHER PUBLICATIONS

Knimetv (2012): www.youtube.com/watch?v=ft7Ksgss3Tc.
A. Tiwari et al., "Workflow Based Framework for Life Science Informatics." Computational Biology and Chemistry, vol. 31, pp. 305-319, 2007.

\* cited by examiner

| POC DEVICE TYPE | DEFINITION OBJECT SEQUENCE | INSTANTIATION PARAMETERS |
|---|---|---|
| A | A, B, C, C, C, C, D | V, W, X, Y, Z |
| B | A, B, C, C, C, D | L, W, X, Y, Z |
| C | A, E, F | L, M, N, O |

Figure 10

SYSTEM AND METHOD FOR GENERATING PATIENT TEST DATA PROCESSING CODE

FIELD OF THE INVENTION

The present invention generally relates to a system and method for generating code for processing patient test data from point of care devices.

BACKGROUND OF THE INVENTION

Point-of-care testing (POCT) is medical testing at or near the site of patient care. The driving notion behind POCT is to bring the test conveniently and immediately to the patient. This increases the likelihood that the patient, physician, and care team will receive the results quicker, which allows for immediate clinical management decisions to be made. POCT includes: blood glucose testing, blood gas and electrolytes analysis, rapid coagulation testing, rapid cardiac markers diagnostics, drugs of abuse screening, urine strips testing, pregnancy testing, faecal occult blood analysis, food pathogens screening, haemoglobin diagnostics, infectious disease testing and cholesterol screening.

POCT is often accomplished through the use of transportable, portable, and handheld instruments (e.g., blood glucose meter, nerve conduction study device) and test kits. Small bench analysers or fixed equipment can also be used when a handheld device is not available—the goal is to collect the specimen and obtain the results in a very short period of time at or near the location of the patient so that the treatment plan can be adjusted as necessary before the patient leaves. Cheaper, smaller, faster, and smarter POCT devices have increased the use of POCT approaches by making it cost-effective for many diseases, such as diabetes, carpal tunnel syndrome (CTS) and acute coronary syndrome.

There is a desire to get output of a POCT device made available immediately within an electronic medical record. The advantage of such integration into electronic medical health records is that results can be shared instantaneously with all members of the medical team through the software interface enhancing communication by decreasing turn-around time (TAT). Also, errors caused by manual input are avoided. One of the challenges accompanying the use of POCT is the plethora of devices and tests which brings with it a high degree of complexity in integrating the POCT devices due to the lack of any agreed standard for data output from such devices.

SUMMARY OF THE INVENTION

One aspect of the invention provides a computer system for generating code for use in processing patient test data from point of care devices, the computer system comprising object definition storage storing a plurality of definition objects, each definition object defining a generic function to be performed in response to an output of a point of care device; instantiation data storage storing instantiation data for use in instantiating definition objects as processing objects for specific functions to be performed in response to outputs from specific point of care devices; and a code generating processor for generating code for at least one processing object to perform at least one specific processing function to process an output from a point of care device by accessing at least one definition object in the object definition storage and the instantiation data in the instantiation data storage to instantiate the at least one definition object using instantiation data for the point of care device.

Another aspect of the invention provides a method of generating code for use in processing patient test data from point of care devices, the method comprising generating code for at least one processing object to perform at least one specific processing function to process an output from a point of care device using at least one definition object and instantiation data to instantiate the at least one definition object using instantiation data for a specific point of care device, each definition object defining a generic function to be performed in response to an output of a point of care device, the instantiation data comprising parameters for instantiating definition objects as processing objects for specific functions to be performed in response to outputs from specific point of care devices; and storing the generated code.

Another aspect of the invention provides a computer system for generating code for use in processing patient test data from point of care devices, the computer system comprising object definition storage storing a plurality of definition objects, each definition object defining a generic function to be performed in response to an output of a point of care device; an interface for receiving instantiation data for use in instantiating definition objects as processing objects for specific functions to be performed in response to outputs from specific point of care devices; and a code generating processor for generating code for at least one processing object to perform at least one specific processing function to process an output from a point of care device using at least one definition object in the object definition storage and the received instantiation data to instantiate the at least one definition object using instantiation data for the point of care device.

Another aspect of the invention provides a medium carrying data for use in generating code for processing patient test data from point of care devices, the medium carrying data comprising a plurality of definition objects, each definition object defining a generic function to be performed in response to an output of a point of care device; and instantiation data for use in instantiating definition objects as processing objects for specific functions to be performed in response to outputs from specific point of care devices.

BRIEF DESCRIPTION OF THE DRAWINGS

FIG. 10 is a diagram illustrating the data stored in a data medium for generating code for processing patient test data from point of care devices according to one embodiment;

DETAILED DESCRIPTION OF EMBODIMENTS

Figure 1:
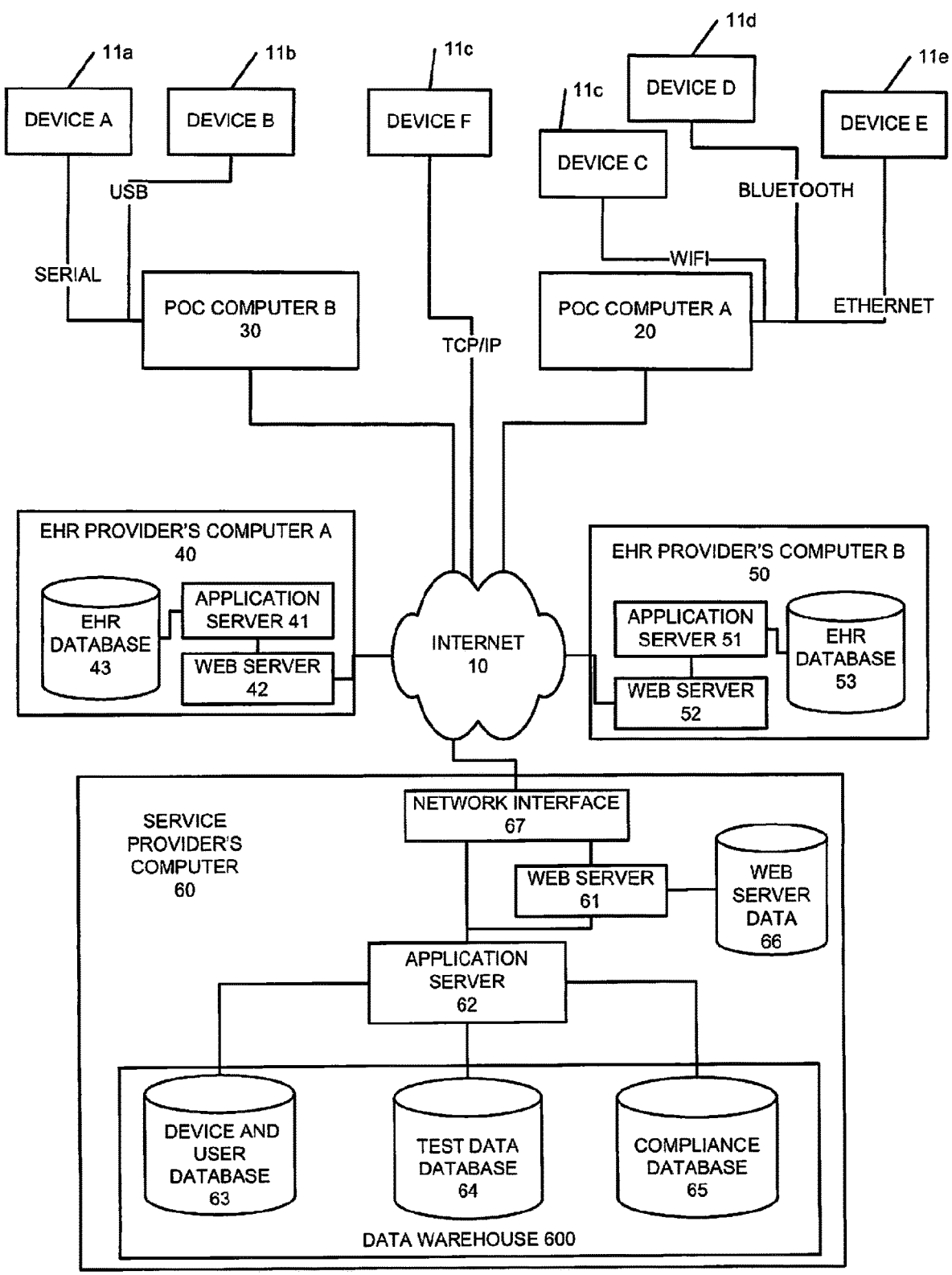
FIG. 1 is a schematic diagram of a system for processing patient test data according to one embodiment.

A first generalised embodiment comprises a computer system for generating code for use in processing patient test data from point of care devices, the computer system comprising object definition storage storing a plurality of definition objects, each definition object defining a generic function to be performed in response to an output of a point of care device; instantiation data storage storing instantiation data for use in instantiating definition objects as processing objects for specific functions to be performed in response to outputs from specific point of care devices; and a code generating processor for generating code for at least one processing object to perform at least one specific processing function to process an output from a point of care device by accessing at least one definition object in the object definition storage and the instantiation data in the instantiation data storage to instantiate the at least one definition object using instantiation data for the point of care device.

As used herein, patient test data comprises any data output from point of care devices, including test data for a patient test, calibration data from the calibration of the point of care device and any other data output from the point of care device for regulatory or safety purposes.

In one embodiment, the instantiation data includes data identifying a sequence of said definition objects for at least one said point of care device.

In one embodiment, the instantiation data includes parameters related to the data expected to be output from the at least one point of care device and the data expected to be received by the at least one point of care device by the or each processing object in the course of the output of a set of point of care data for a patient test.

In one embodiment, the computer system includes an interface for communication with a point of care device, and a user interface for receiving instantiation parameters and definition object selections from a user; wherein the code generating processor is adapted to generate code for at least one processing object according to the received instantiation parameters and definition object selections, and to run the generated code to attempt to process patient test data received from the point of care device; wherein the user interface is adapted to display result of the processing and to receive revised instantiation parameters and definition object selections from the user for generation and running of revised code by the code generating processor.

In one embodiment, the computer system includes a communication interface for transmitting the instantiation parameters to a point of care computer for storage at the point of care computer and for use at the point of care computer in generating code for at least one processing object to perform at least one specific processing function to process an output from a point of care device by accessing at least one stored definition object and the instantiation data to instantiate the at least one definition object using instantiation data for the point of care device.

In one embodiment, the computer system includes a communication interface for transmitting the generated code for at least one point of care device to a point of care computer for the storage and running of the code to process patient test data received at the point of care computer from a point of care device.

In one embodiment, the computer system includes an interface to receive patient test data from a point of care device, and a data processor for running the generated code to process the patient test data received from the point of care device.

A second generalised embodiment provides a method of generating code for use in processing patient test data from point of care devices, the method comprising generating code for at least one processing object to perform at least one specific processing function to process an output from a point of care device using at least one definition object and instantiation data to instantiate the at least one definition object using instantiation data for a specific point of care device, each definition object defining a generic function to be performed in response to an output of a point of care device, the instantiation data comprising parameters for instantiating definition objects as processing objects for specific functions to be performed in response to outputs from specific point of care devices; and storing the generated code.

In one embodiment, the instantiation data includes data identifying a sequence of said definition objects for at least one said point of care device.

In one embodiment, the instantiation data includes parameters related to the data expected to be output from the at least one point of care device and the data expected to be received by the at least one point of care device by the or each processing object in the course of the output of a set of point of care data for a patient test.

In one embodiment, the method includes receiving instantiation parameters and definition object selections from a user interface; generating the code for at least one processing object according to the received instantiation parameters and definition object selections, attempting to run the code to process patient test data received from the point of care device; displaying a result of the processing; receiving revised instantiation parameters and definition object selections from the user interface; and generating and running revised code for at least one processing object according to the revised instantiation parameters and definition objects.

In one embodiment, the method includes transmitting the instantiation parameters to a point of care computer for storage at the point of care computer and for use at the point of care computer in generating code for at least one processing object to perform at least one specific processing function to process an output from a point of care device by accessing at least one stored definition object and the instantiation data to instantiate the at least one definition object using instantiation data for the point of care device.

In one embodiment, the method includes transmitting the generated code for at least one point of care device to a point of care computer for the storage and running of the code to process patient test data received at the point of care computer from a point of care device.

In one embodiment, the method includes receiving patient test data from a point of care device, and a data processor for running the generated code to process the patient test data received from the point of care device.

A third generalised embodiment provides a computer system for generating code for use in processing patient test data from point of care devices, the computer system comprising object definition storage storing a plurality of definition objects, each definition object defining a generic function to be performed in response to an output of a point of care device; an interface for receiving instantiation data for use in instantiating definition objects as processing objects for specific functions to be performed in response to outputs from specific point of care devices; and a code generating processor for generating code for at least one processing object to perform at least one specific processing function to process an output from a point of care device using at least one definition object in the object definition storage and the received instantiation data to instantiate the at least one definition object using instantiation data for the point of care device.

In one embodiment, the instantiation data includes data identifying a sequence of said definition objects for at least one said point of care device.

In one embodiment, the instantiation data includes parameters related to the data expected to be output from the at least one point of care device and the data expected to be received by the at least one point of care device by the or each processing object in the course of the output of a set of point of care data for a patient test.

A fourth generalised embodiment provides a medium carrying data for use in generating code for processing patient test data from point of care devices, the medium carrying data comprising a plurality of definition objects, each definition object defining a generic function to be performed in response to an output of a point of care device; and instantiation data for use in instantiating definition objects as processing objects for specific functions to be performed in response to outputs from specific point of care devices.

In one embodiment a non-transient storage medium stores computer readable code for controlling a computer to carry out any of the methods as described above.

In one embodiment a carrier medium carries computer readable code for controlling a computer to carry out any of the methods as described above.

In the following detailed description, reference is made to the accompanying drawings that form a part hereof, and in which is shown by way of illustration specific embodiments in which the inventive subject matter may be practiced. These embodiments are described in sufficient detail to enable those skilled in the art to practice them, and it is to be understood that other embodiments may be utilized and that structural, logical, and electrical changes may be made without departing from the scope of the inventive subject matter. Such embodiments of the inventive subject matter may be referred to, individually and/or collectively, herein by the term "invention" merely for convenience and without intending to voluntarily limit the scope of this application to any single invention or inventive concept if more than one is in fact disclosed.

The following description is, therefore, not to be taken in a limited sense, and the scope of the inventive subject matter is defined by the appended claims.

The functions or algorithms described herein are implemented in hardware, software or a combination of software and hardware in one embodiment. The software comprises computer executable instructions stored on computer readable media such as memory or other type of storage devices, or any other form of media such as a signal. Further, described functions may correspond to modules, which may be software, hardware, firmware, or any combination thereof. Multiple functions are performed in one or more modules as desired, and the embodiments described are merely examples. The software is executed on a digital signal processor, ASIC, microprocessor, or other type of processor operating on a system, such as a personal computer, server, a mobile device, or other device capable of processing data including network interconnection devices. The network can comprise a wired or wireless network and includes a private network, a virtual private network (VPN), a Local Area Network (LAN), a Wide Area Network (WAN) and the internet for example. Although in the following detailed embodiment the interconnection between computers is shown over the internet, the invention encompasses any form of network connection.

Some embodiments implement the functions in two or more specific interconnected hardware or software modules or devices with related control and data signals communicated between and through the modules, or as portions of an application-specific integrated circuit. Thus, the exemplary process flow is applicable to software, firmware, and hardware implementations.

Embodiments of the present invention can be implemented on any form of computing hardware using one or more computer programs or applications (software). The computer program(s) can be provided to a computer on any suitable carrier medium. One such type of medium is a computer storage medium which represents a non-transient medium. Computer storage media include random access memory (RAM), read only memory (ROM), erasable programmable read-only memory (EPROM) and electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions. Another form of medium is a transient medium such as a signal. A signal can comprise an electrical signal over a wire, an electromagnetic signal transmitted over a wire or wirelessly, an optical signal, an acoustic signal, or even a magnetic signal. Once common form of signal is transmitted over a communication network, which can be wired or wireless or a combination of both, e.g. a local area network (LAN), a wide area network (WAN) or the internet.

The point of care devices can comprises any device for carrying out any patient medical test at a point of care facility or even at the patients premises, such as blood glucose testing, blood gas and electrolytes analysis, rapid coagulation testing, rapid cardiac markers diagnostics, drugs of abuse screening, urine strips testing, pregnancy testing, faecal occult blood analysis, food pathogens screening, haemoglobin diagnostics, infectious disease testing and cholesterol screening. The medical test data can also include patient vitals such as blood pressure and heart rate and patient data such as height, weight, age etc. A point of care facility can comprise any medical facility capable of providing such patient tests and test data such as a doctor's surgery, a clinic, or a specialist centre. Where a point of care device is used by a patient in their own facilities either by themselves or by a visiting medical practitioner, the patient test data can be obtained as an output from the device on a storage media for later upload to a point of care computer, or as a signal to be transmitted over a communications network (wired or wireless) to the point of care computer. A point of care computer is generally a computer provides at the point of care facility for direct connection to the point of care devices. However, the point of care computer can be any computer connected by a suitable communication connection to the point of care device or devices for the reception of patient test data from the point of care device. Such a communication connection can be via intermediary networks and computers which perform no processing of the patient test data. The processing of the patient test data and two way communication with point of care device is achieved using the program code in the point of care computer. The point of care computer can hence comprise a client in a computer network or a server.

There are no standards covering the format of the data output from points of care devices. Each device can output data in a proprietary format dependent upon a manufacturer and/or a type of point of care device (i.e. the type of patient test). Point of care devices provide data outputs which can require two way communication between a point of care computer connected to the point of care device during the data output and can provide a communication in the form of a communication pattern or sequence of data packages or communication messages. The individual packages, messages or parts can themselves conform to a pattern or structure which can be classified or defined generically for a number of specific data packages, messages or parts of an output for a number of point of care devices.

A generalised embodiment provides a library of definition objects which have been developed by system developers to define a generalised function or function relating to processing an output of a point of care device. The processing can comprise a simple handshake e.g. responding to an enquiry with an acknowledgement or more complex processing which can include the storage of a package of data (the message payload). The precise form of the message protocol for point of care devices is not included in the definition objects. The details of this are separately defined for each point of care device in the form of object instantiation parameters. In this way the combination of a generic definition object with instantiation parameters, provides the necessary logic for processing a part (or the whole) of a communication from a point of care device. The instantiation parameters can also include information identifying a sequence of definition objects required for the instantiation of a complete communication output from a point of care device. Thus the library of definition objects can include the code required for the generation of building of code for a plurality of point of care devices simply by instantiation the definition objects. Hence the definition objects act as the building blocks for the formation of code for the processing of communications with point of care devices. This reduces the requirement for new code to be developed every time a new point of care device is required to be interfaced to a point of care computer to upload the patient test data there from. Also, the storage of parameters with a generalised set of definition objects reduces provides for efficient storage. It is not necessary to store a complete set of code for each point of care device. Code from the library can be reused as generalised definition objects. Code for each point of care device can be efficiently generated or built using the code object blocks.

In one embodiment, to avoid the need to transmit code from a server such as a centralised service or development server, the point of care computer can be provided with the library of definition objects and only the instantiation parameters need be transmitted over the network for instantiating the definition objects to generate code to configure the point of care computer to process data from point of care devices.

Embodiments of the invention can be implemented with the systems and methods disclosed in U.S. patent application Ser. No. 14/462,722 filed on 19 Aug. 2014, and co-pending application number GB 2533910 A filed herewith by the same applicants and entitled "Wireless processing unit and method for collecting patient test data from point of care devices", the contents of both of which are hereby incorporated in their entirety by reference.

A first embodiment of the present invention will now be described with reference to FIG. 1.

FIG. 1 schematically illustrates a patient test data gathering and processing system. Point of care devices 11*a* to 11*d* are provided to obtain patient test data. The point of care devices 11*a* to 11*f* are connected to interfaces in respective point of care (POC) computers 20 and 30. The POC computers 20 and 30 are provided at POC facilities or accessible to POC facilities. The POC devices 11*a* to 11*f* may be present at the POC facility or used at a remote location when portable e.g. at the patients premises or in a mobile facility. The POC devices 11*a* to 11*f* generate output patient test data as a result of a test being performed by an operator on a patient. The patient test data can be output using any known convenient method which depends upon the output capabilities of the POC device and includes:

From POC device A (11*a*) over a serial computer line to a serial computer port in the POC computer 30

From POC device B (11*b*) over a USB link to a USB computer port in the POC computer 30

From POC device C (11*c*) over a wireless Wi-Fi link to a wireless port in the POC computer 20

From POC device D (11*d*) over a Bluetooth® link to a Bluetooth® port in the POC computer 20

From POC device E (11*e*) over an Ethernet line to an Ethernet port in the POC computer 20

From POC device F (11*f*) over an internet connection to a an internet network interface the POC computer 20

From a POC device the patient test data can also be stored onto a storage device such as a solid state memory device, an optical disk or even a magnetic disk to be read by an appropriate storage device in the POC computer.

The POC computer 20 and 30 comprises any suitable computing device such as a general purpose computer, a mobile device, a laptop, tablet computer etc. The POC computer 20 and 30 has a connection via a network interface to the internet 10 over a wired or wireless network to provide access to send and receive data over a network such as the internet 10.

Electronic health records (EHR) are stored and maintained by EHR providers. There are a number of such providers available and different medical care providers use different EHR providers. The EHR providers host the EHR records in databases 43 and 53 on computers 40 and 50. Each EHR provider's computer 40 and 50 implements a web server 42 and 52 for interfacing via a network interface to the internet 10 and an application server 41 and 51 for providing the required functionality and interface to the respective EHR databases 43 and 53.

In this embodiment, the patient test data processing is hosted in a service provider's computer 60 comprising a server system implementing a Software as a Service model, where a 'thin client' in the form of a client application is implemented on each POC computer 20 and 30. On the service provider's computer 60 web services are implemented to provide the functionality. On the POC computer 30 and 30a Windows® service is implemented to provide the functionality.

As shown in FIG. 1 schematically, a web server 61 is provided with access to web server data 66 to provide a web interface to the POC computers 20 and 30. This enables an operator to login into the service and interact with interfaces generated by the web server 61 e.g. to view lists of and select cached patient test data, to input any required additional patient test data, to access and input operator qualification data etc. An application server 62 is provided to provide the functionality and access the device and user database 63, the test data database 64 and the compliance database in the data warehouse 600. Both the application server 62 and the web server 61 are connected by a network interface 67 to the internet 10.

In the embodiment illustrated in FIG. 1, the system operates such that the operators of the POC devices 11a to 11f and the POC computers 20 and 30 require access to the EHR records hosted by the EHR provider's computers 40 and 50 i.e. the POC facility does not have its own proprietary EHR and instead access EHR providers available to many POC facilities and providers.

Figure 2:
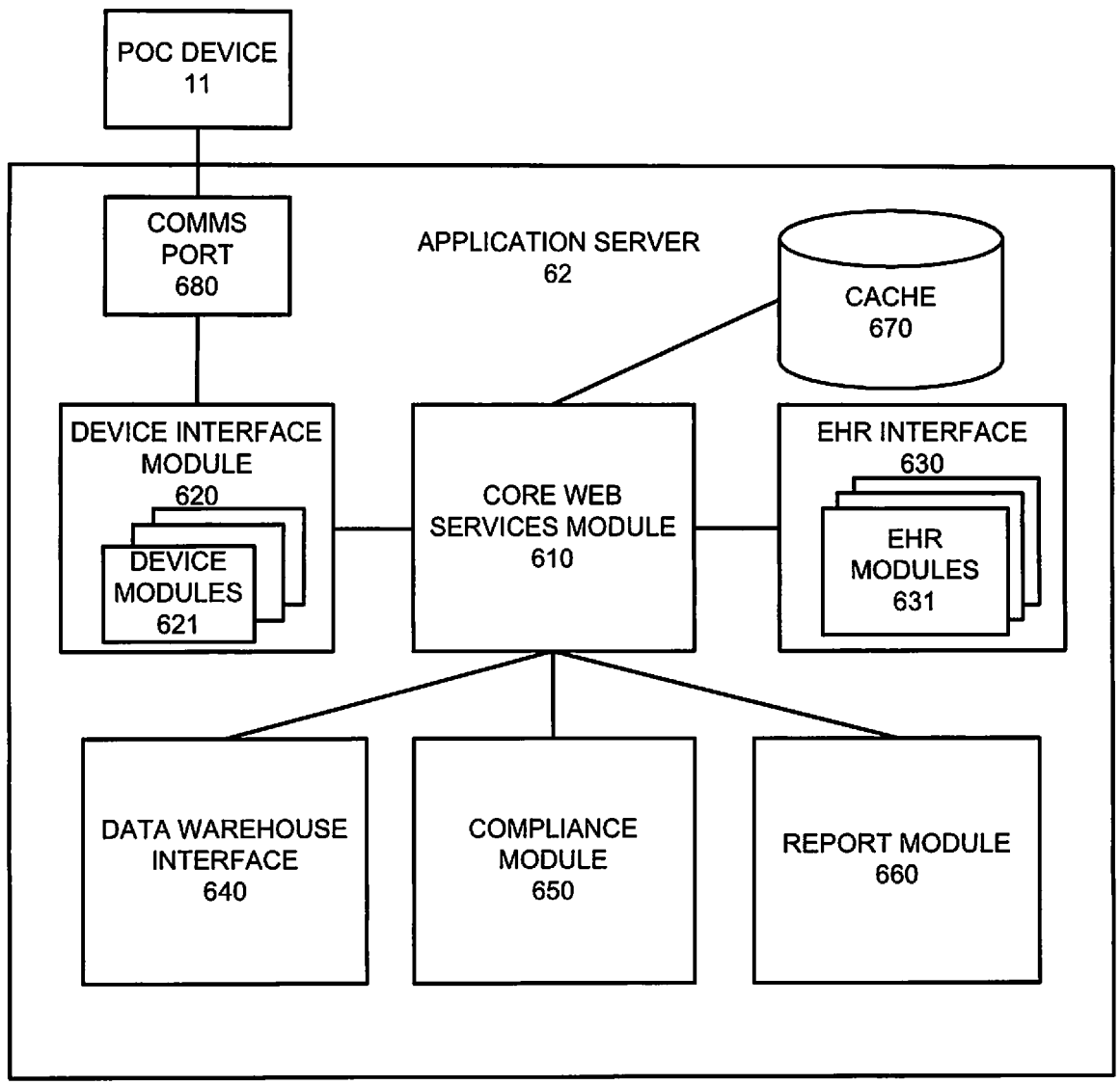
FIG. 2 is a schematic diagram of the details of the application server of FIG. 1 according to one embodiment.

FIG. 2 is a schematic diagram of the application server 62 of the embodiment of FIG. 1, hosted on the service provider's computer system 60 according to one embodiment. The application server 62 operates a core web services module 610 which has access to a cache memory 670 for temporary storage of patient test data pending approval and completion by operators, and which provides an interface 640 to a data warehouse 600. A compliance module 650 is implemented to provide regulatory compliance functionality. A reports module 660 is provided to enable users of the service with access to reports on patient tests and compliance. A device interface module 620 is provided which implements specific device modules 621 dependent upon the identity of the devices detected in the patient test data. The device modules 621 receive the patient test data and perform device specific processing on it, namely the data which is in a format specific to the device is parsed using a parser specific to the device to reformat the data according to a test type object dependent upon the test type identified for the patient test data. The patient test data reformatted according to the identified test type can then be stored in the cache 670 pending approval and completion by the operator. An EHR interface 630 is also provided and implements EHR modules 631 which are specific to the EHR provider to which the patient test data is to be transmitted. The EHR provider can be identified from an order identifier associated with the patient test. When a medical practitioner places an order for a POCT in an EHR, the order is assigned a unique identifier and it is associated with the patient record and patient identifier in the EHR. When a patient test is performed an operator will input a patient name or identifier enabling the order to be found in the EHR and hence associated with the patient test data in the cache 670 of the service provider's computer 60 pending completion and acceptance of the patient test data by the operator. In an alternative embodiment, for some patient test data, such a patient vitals (e.g. heart rate, blood pressure), there may be no order in the EHR system. In this embodiment, a patient record in the EHR can be identified from a patient ID or name and the test data can be pushed up to the EHR provider's computer 40 and 50 for storage of the test data in the EHR record for the patient in the EHR database.

The device modules 621 comprise code capable of recognising the messages from the POC devices. Parsing is performed by the device modules 621 by taking the patient test data from the POC device and formatting the patient test data according to a test type determined from a test type library on the basis of the POC device name. In other words, each device module 621 is associated with a test type since it is associated with a device type, which can only produce patient test data of a certain test type. More than one device type can be associated with a test type, since different device types could be used to provide a test of the same type e.g. ABC Inc's Blood Monitor is one device type and XYZ's Blood Monitor is another device type but both provide patient test data of the same test type—Blood Test A.

Figure 3:
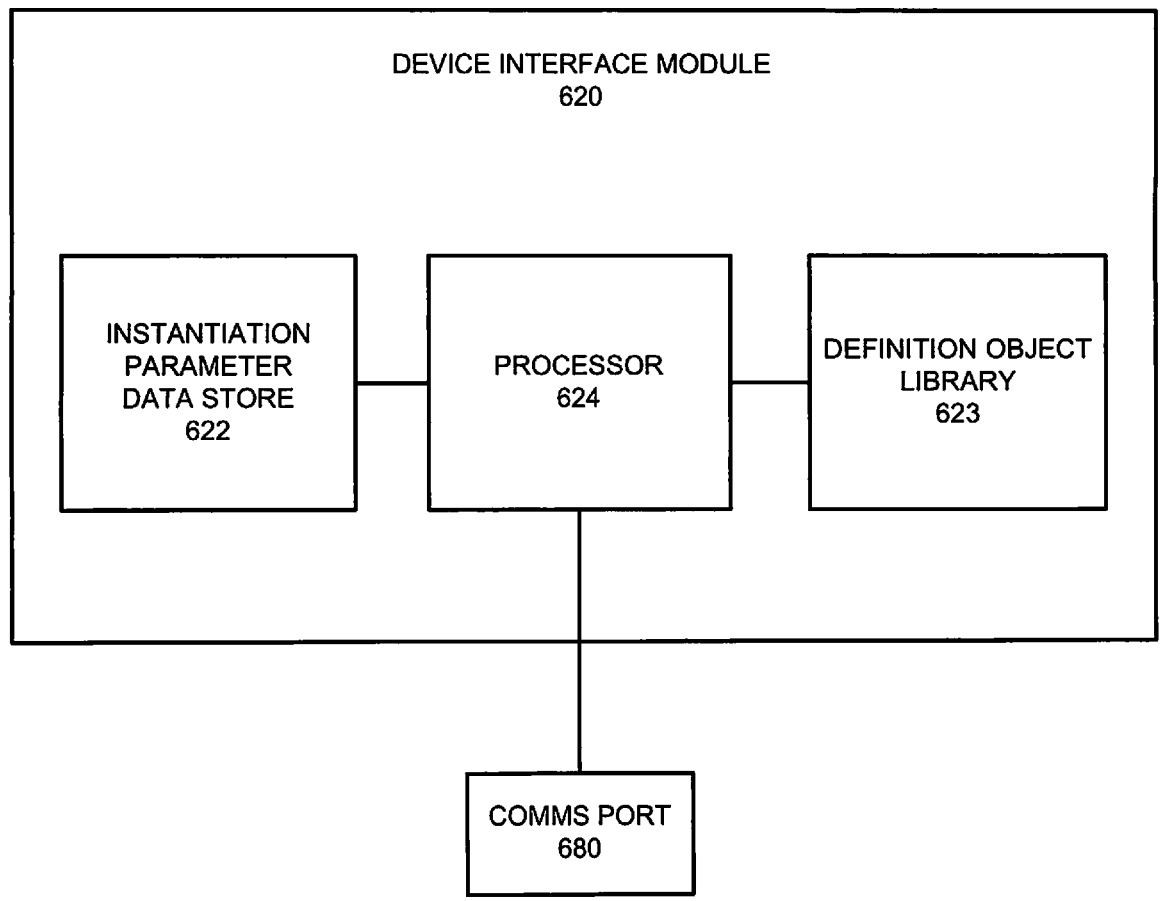
FIG. 3 is a schematic diagram of the details of the device interface module of FIG. 2 according to one embodiment.

FIG. 3 is a schematic diagram of the device interface 620 of FIG. 2 in more detail. A processor 624 is provided to access an object definition library 623 and an instantiation parameter data store 622. A communications port 680 is provided in the service provider's computer 60 to provide communications with a point of care device 11. The processor 624 executes code to execute the device modules 621. The code can be stored in the object definition library 623 as generalised objects with instantiation parameters stored in the parameter data store 622. In this way, the required code for processing data of a test type can be generated by instantiating objects dependent upon the test type. The processor 624 can look up appropriate instantiation parameters for one or more objects based on the test type, which can be indicated in or based on a parameter sent from the point of care device. The instantiation parameters can include parameters identifying the objects and any order of implementation of the objects for the ordered processing of the patient test data.

The processor 624 is also operable to enable a user to access the object definition library 623 via the core web services module 610 using a web browser to be able to select of add objects and to access the instantiation parameter data store 622 to select and change or add instantiation parameters in a development process which will be described in more detail herein after with reference to FIGS. 5 and 6.

Figure 4:
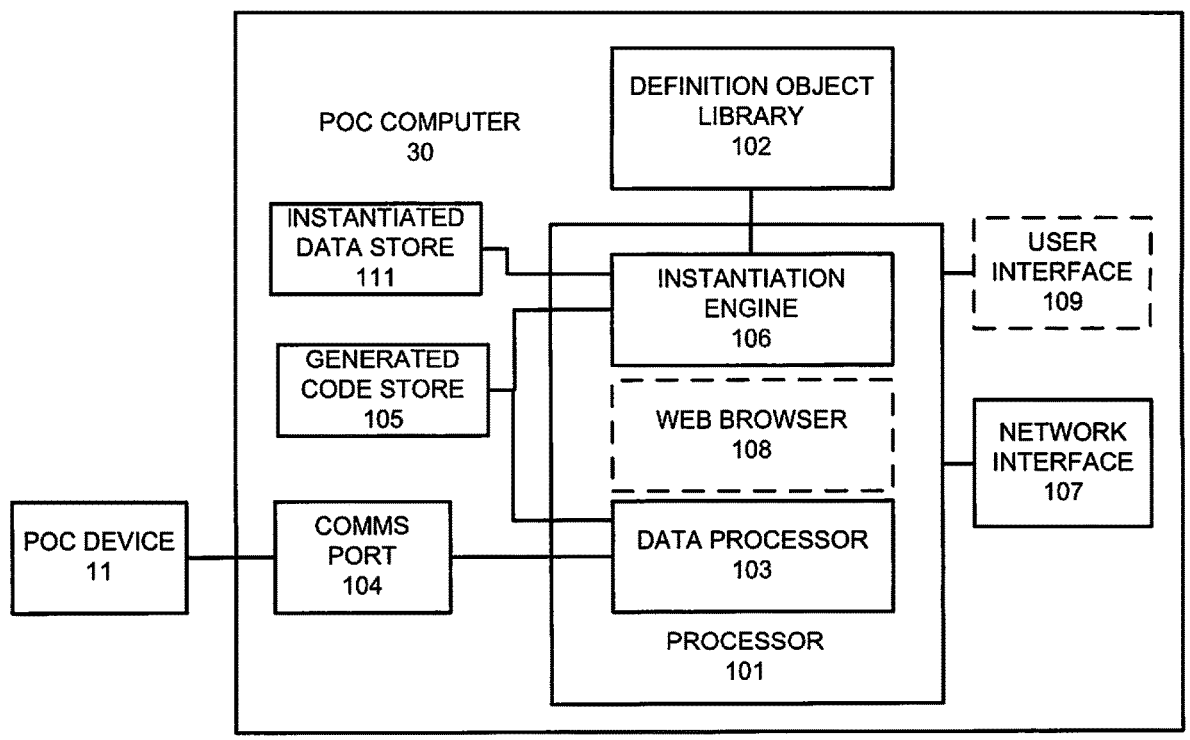
FIG. 4 is a schematic diagram of a point of care (POC) computer according to one embodiment.

FIG. 4 is a schematic diagram of a point of care computer 30 according to one embodiment. The POC computer is illustrated as just connected to one POC device. Of course, as shown in FIG. 1, it can be connected to many.

A processor 101 of the POC computer 30 executes code to implement a data processor 103 for receiving and sending communications from and to the POC device 11 via a communications port 104. The data processor 103 performs the process of communications control to control the reception and transmission of communications to the POC device 11 and the transmission and reception of communications over a network interface 107 to the service provider's computer 60.

A definition object library 102 is provided storing the definition objects which can be used to generate or build the code for controlling communications with a POC device 11 i.e. processing patient test data output from the POC device 11. An instantiation data store 111 is also provided for storing instantiation parameters for definition objects for the generation or building of processing code for specific POC devices. The processor 1010 executes code to implement an instantiation engine for the generation of code by the instantiation of definition objects. The generated code is stored in the generated code store 105 for reading and execution by the data processor 103. The processor 101 can also execute code to implement a web browser 108 to provide a user with an interface to the functions of the service provider's computer. In such an embodiment, the POC computer is provided with a user interface 109 to enable the input and output of information e.g. a display, keyboard, a pointing device, a touch sensitive display etc. However, it is not required for the POC computer to have any user interface 109 (and hence no web browser 108). The POC computer can simply be connected over a network to the service provider's computer 60. The provision of the instantiation parameters can be by download from the service provider's computer 60.

Hence, in the embodiment of FIG. 4, the POC computer is provided with the definition object library 102 to enable it to build or generate any POC device processing code for controlling communications with the POC device to capture the output data and pass it onto the service provider's computer 60. Instantiation data is all that is required to enable the building or generation of the required code to process the output of a required POC device.

Figure 5:
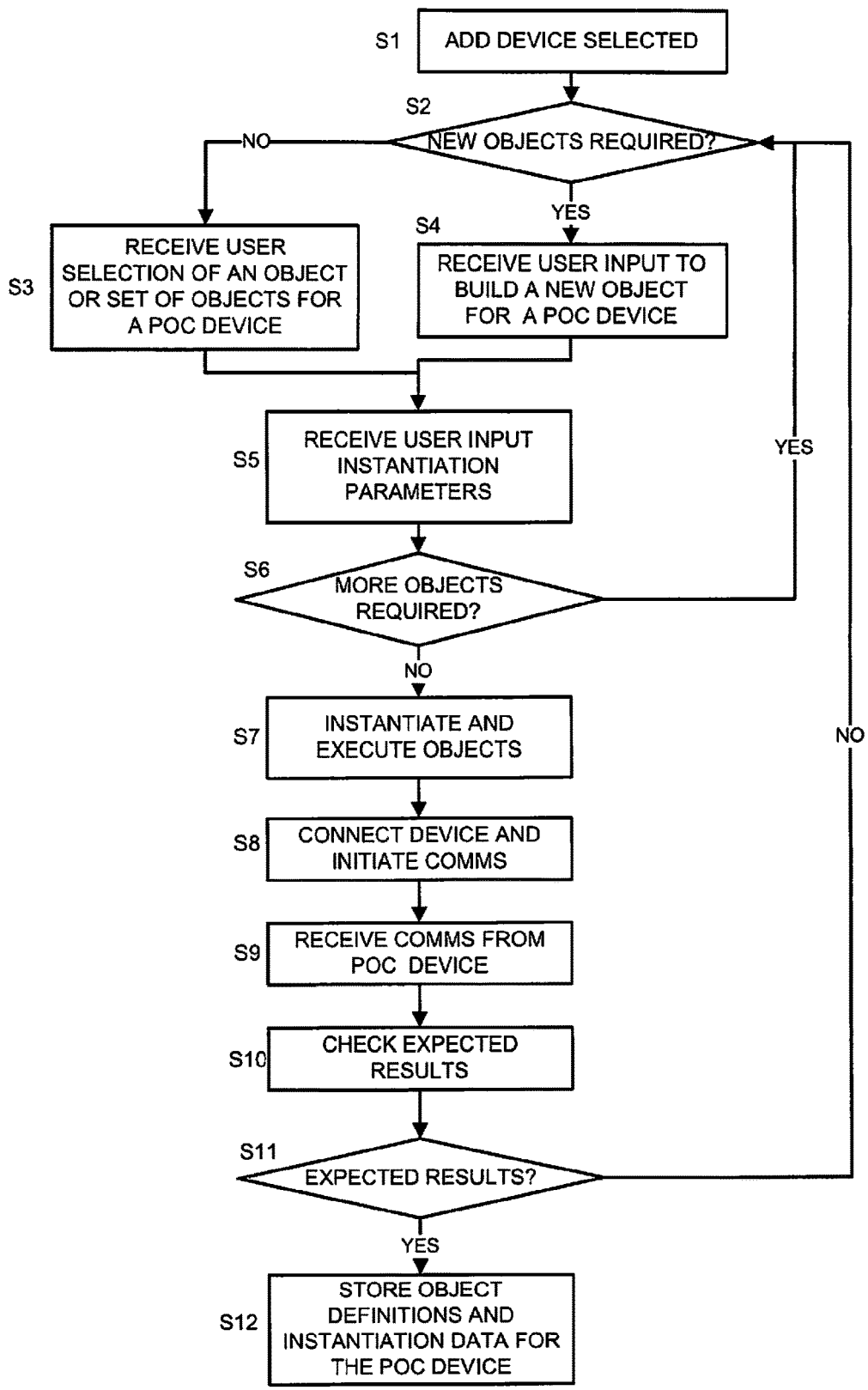
FIG. 5 is a flow diagram illustrating the process on a server to develop object definitions and instantiation data for POC devices according to one embodiment.

FIG. 5 is a flow diagram illustrating the process to develop definition object and instantiation parameters for POC devices according to one embodiment. The process can be implemented on the service provider's computer 60 or a separate development server 70 as will be described herein after with reference to FIG. 11. The process is hence run by a developer of POC device specific interface code.

In step S1a user selects to add new interface code specific to a new POC device. The user can select in step S2 whether to select one or a set of definition objects currently available in the definition object library 623 (step S3) or to input information to build a new object for a POC device (step S4). The building of a new definition object can comprise entering code or using a code building interface. In step S5 user input instantiation parameters are received and the process loops at step S6 until all the required definition objects and instantiation parameters have been input or selected.

In step S7 the definition objects are instantiated and executed and in step S8 the POC device 11 is connected to the communication port 680 and a patient test data transmission output is initiated. The communications from the POC device are received at the POC computer in step S9 and the developer checks to determine whether the resulting data is what is expected from the POC device (step S10). If not, the process returns to step S2 to repeat the process until the expected results are achieved and hence the correct definition objects and instantiation parameters have been developed. These are then stored in step S12.

Figure 6:
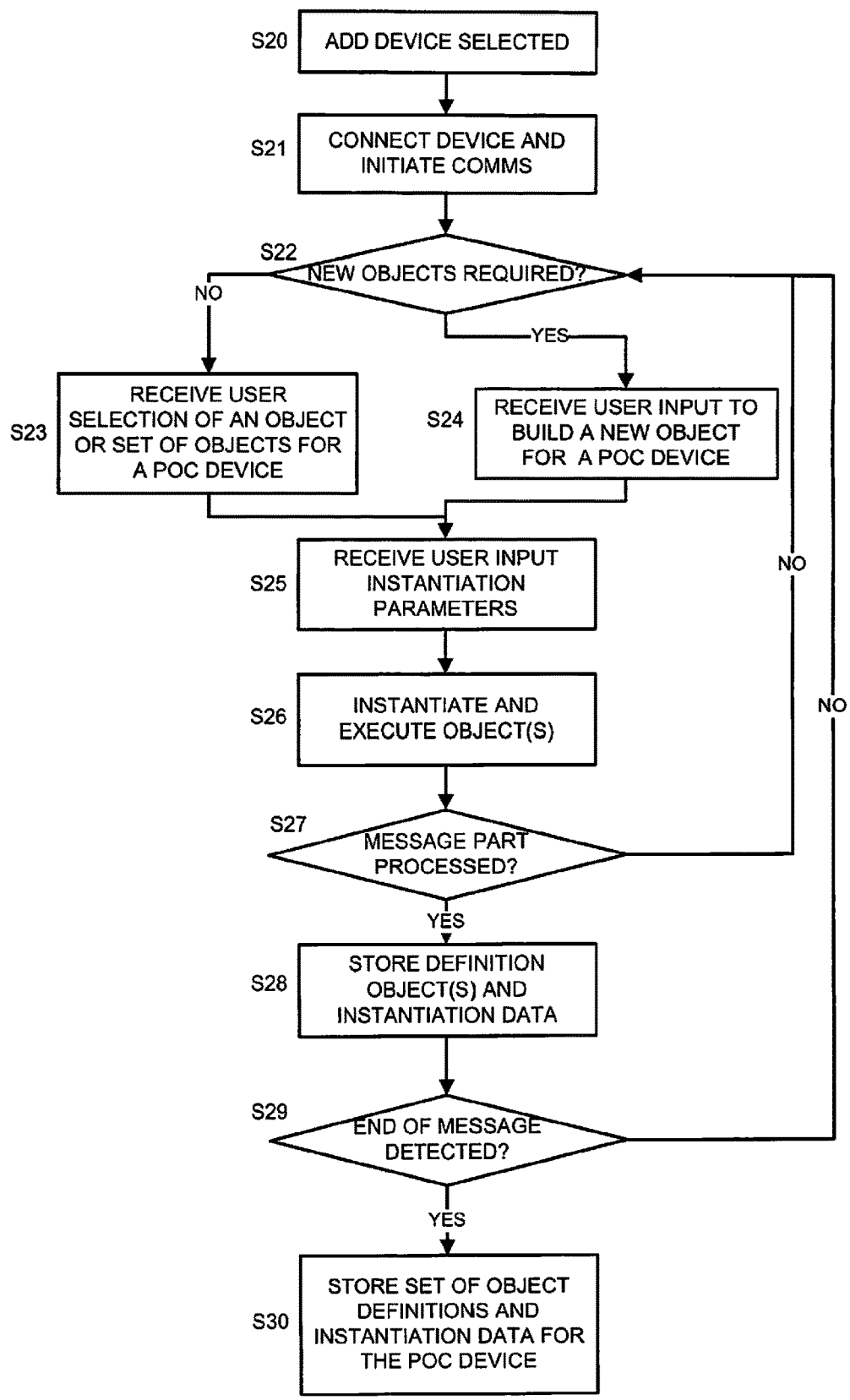
FIG. 6 is a flow diagram illustrating the process on a server to develop object definitions and instantiation data for POC devices according to another embodiment.

FIG. 6 illustrates an alternative development process to that of FIG. 5, in which the developed code is tested on the fly, object by object (function by function).

In step S20a user selects to add new interface code specific to a new POC device. The communications from the POC device are received at the POC computer in step S21. The user can select in step S22 whether to select one or a set of definition objects currently available in the definition object library 623 (step S23) or to input information to build a new object for a POC device (step S24). The building of a new definition object can comprise entering code or using a code building interface. In step S25 user input instantiation parameters are received. In step S26 the definition object(s) are instantiated and executed and if the part of a message is processed, the process loops at step S27 until all the required definition objects and instantiation parameters have been input or selected for a message part. In step S28 the definition object(s) and the instantiation data is stored for the message part. In step S29 it is then determined whether the message from the POC device is complete (i.e. all message parts processed) and if not the process loops back to step S22 until all are completed. The definition objects and instantiation parameters are then stored in step S30.

The process of FIG. 5 or 6 enable developers to develop POC device code to be downloaded to POC computers either in the form of instantiation parameters or even as full sets of code build using the instantiation parameters and the definition objects at the server, as will be described in more detail herein after.

Examples of POC device code implementation and the related instantiation data and definition objects will now be described with reference to FIGS. 7 to 10.

Figure 7:
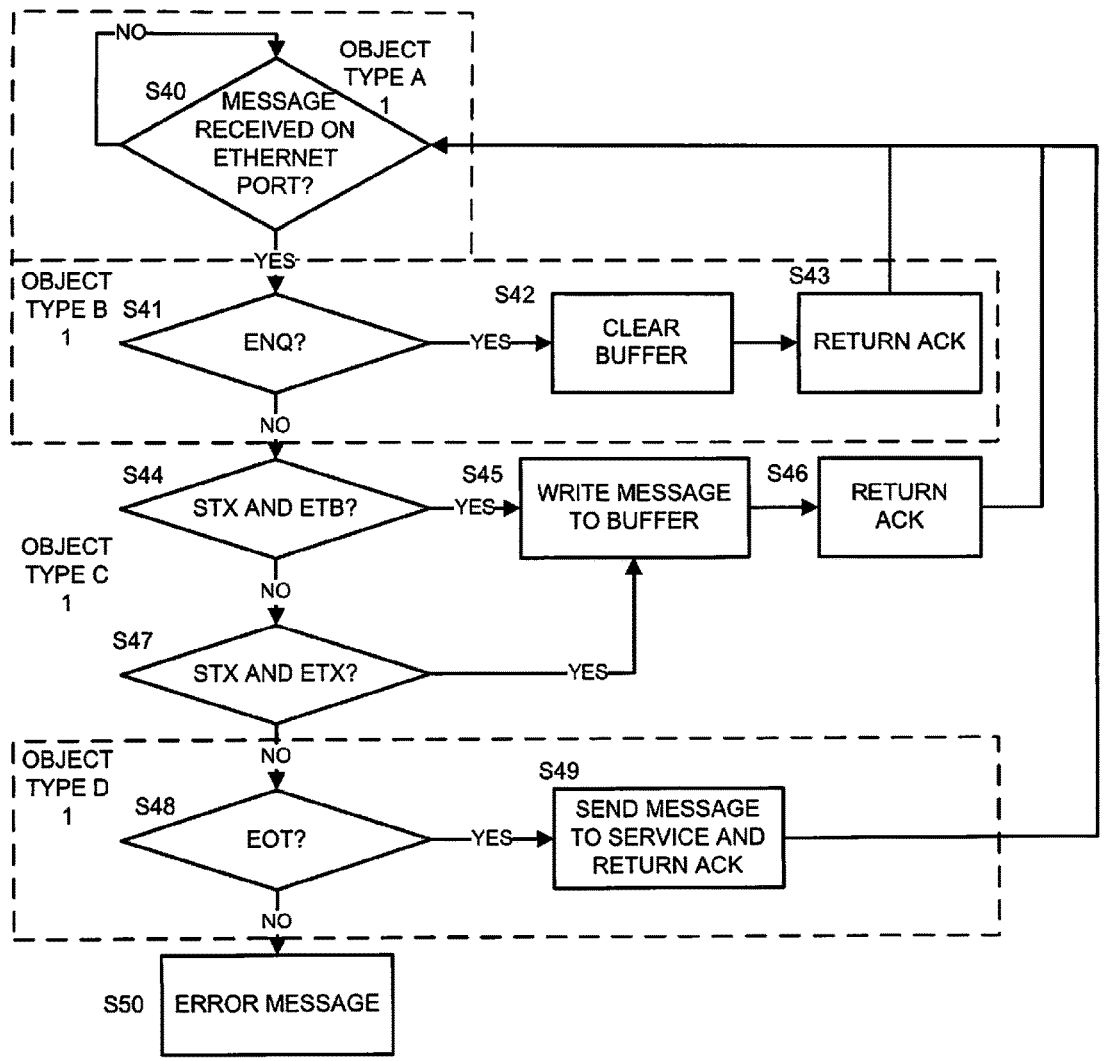
FIG. 7 is a flow diagram illustrating the process for processing patient test data from a point of care device of a first type according to one embodiment.

FIG. 7 illustrates a process implemented by processing code for processing data from a POC device of type A. In this embodiment, the POC device communicates using the ASTM communication protocol. A typical communication session to output a message comprises a plurality of message parts as shown in table 1 below. The communication between the POC device and the POC computer is two way. The POC computer must transmit an <ACK> character at the end of receipt of each message part to prompt the POC device to send the next.

TABLE 1 the ASTM communication protocol

| Sender (PCC) | Direction | Receiver (LIS) | Description |
| --- | --- | --- | --- |
| <ENQ> | --> | | Notifying receiver that there is information to send. |
| | <-- | <ACK> | LIS sends back an ACK. if it is ready. |
| <STX>1H Message<ETX><CS><CR><LF> | --> | | Header record |
| | <-- | <ACK> | |
| <STX>2P Message<ETX><CS><CR><LF> | --> | | Patient record |
| | <-- | <ACK> | |
| <STX>3O Message<ETX><CS><CR><LF> | --> | | Order record |
| | <-- | <ACK> | |
| <STX>4R Message<ETX><CS><CR><LF> | --> | | First result record |
| | <-- | <ACK> | |
| <STX>5R Message<ETX><CS><CR><LF> | --> | | Second result record |
| | <-- | <ACK> | |
| . | | | |
| . | | | |
| . | | | |
| <STX>?L Message<ETX><CS><CR><LF> | --> | | Terminator record |

TABLE 1-continued the ASTM communication protocol

| Sender (PCC) | Direction | Receiver (LIS) | Description |
|---|---|---|---|
|  | <-- | <ACK> |  |
| <EOT> | --> |  | Message complete transmitted. |

Using this protocol, a partial message can be transmitted with a terminating character <ETB> rather than <ETX> to indicate that the following message part should be concatenated with the current message part.

The communication characters comprise:
<ENQ>—ASCII 0x05
<STX>—ASCII 0x02
<ETX>—ASCII 0x03
<EOT>—ASCII 0x04
<ACK>—ASCII 0x06
<ETB>—ASCII 0x17

In step S40 of FIG. 7 the POC computer waits in a monitoring state to receive a message on an Ethernet port in this embodiment. The function of monitoring a port can be coded as a definition object, e.g. object type A. In this instance the object is instantiated by instantiation data to monitor the Ethernet port and hence it is an object type A instantiation 1. In step S41 the process determines whether the communication is <ENQ> and if so, a temporary storage buffer for message parts is cleared in step S42 and in step S43 the POC computer returns <ACK> and waits for the next message (step S40). This part of the processing by the POC computer comprises the function of identifying the initiating of a message part, clearing the buffer ready to receive the message part and sending an acknowledgement. This function can be coded as a definition object of type B. It is instantiated with parameters such as the initiating character <ENQ> and response character of <ACK> and hence it is an object type B instantiation 1.

If the communication is not <ENQ> and is instead a message part framed by <STX> and <ETB> (step S44) or <STX> and <ETX> (step S47), in step S45 the POC computer writes the message part to the buffer and in step S46 returns <ACK> and waits for the next message (step S40). This part of the processing by the POC computer comprises the function of identifying a frame of a message block, storing it and sending an acknowledgement. This function can be coded as a definition object of type C. It is instantiated with parameters such as the message frame characters <STX> and <ETB> or <STX> and <ETX> and response character of <ACK> and hence it is an object type C instantiation 1. In this embodiment the processing of the message frame part <STX> <ETB> and <STX> <ETX> are defined by the same definition object since the only different is in the instantiation with the frame end character <ETB> and <ETX>. In an alternative embodiment, since the storing of the partial frame terminated with <ETB> requires the concatenation with the next frame, a separate definition object can be defined for this different processing function.

If the communication is <EOT> (step S48), the completed message stored in the buffer is transmitted by the POC computer 30 over the network 10 to the service provider's computer 60 (step S49) and an ACK response is returned to the POC device. The POC computer 30 then waits for the next message (step S40). This function can be coded as a definition object of type D. It is instantiated with parameters such as the character <EOT> and details of the service to which the message is transmitted and the character <ACK> and hence it is an object type D instantiation 1.

If the POC computer detects a message character other than <ENQ>, <STX> or <EOT>, an error message is generated in step S50.

Hence, in this embodiment, the code required by the POC computer 30 to process communications with a POC device 11 is based on the instantiation of four definition objects.

Figure 8:
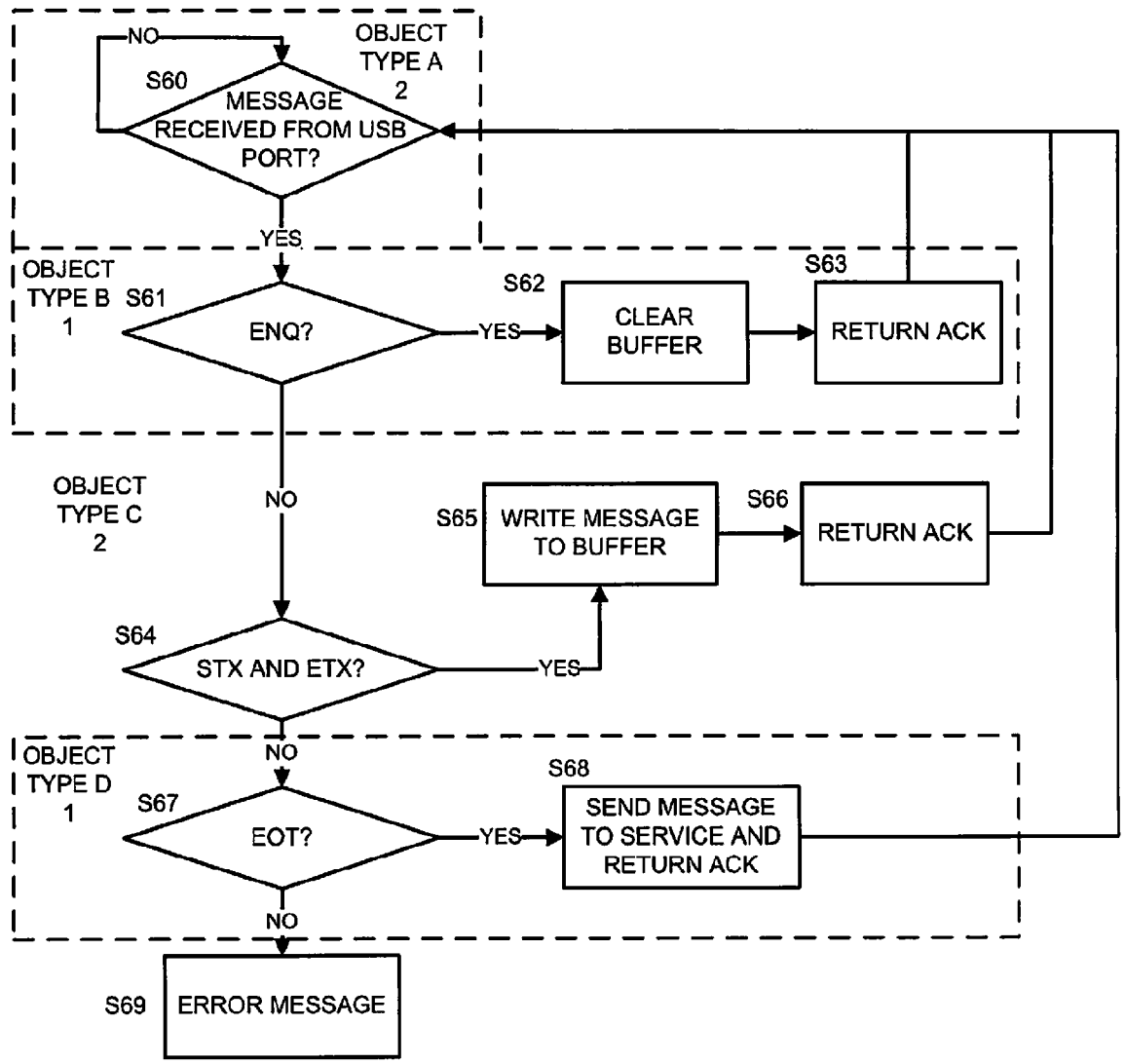
FIG. 8 is a flow diagram illustrating the process for processing patient test data from a point of care device of a second type according to one embodiment.

FIG. 8 illustrates a process implemented by processing code for processing data from a POC device of type B. In this embodiment, like the previous embodiment the POC device communicates using the ASTM communication protocol. As before, the communication between the POC device and the POC computer is two-way. The POC computer must transmit an <ACK> character at the end of receipt of each message part to prompt the POC device to send the next.

In step S60 the POC computer waits in a monitoring state to receive a message on a USB port in this embodiment. The function of monitoring a port can be coded as a definition object, e.g. object type A. In this instance the object is instantiated by instantiation data to monitor the USB port and hence it is an object type A instantiation 2. In step S61 the process determines whether the communication is <ENQ> and if so, a temporary storage buffer for message parts is cleared in step S62 and in step S63 the POC computer returns <ACK> and waits for the next message (step S60). This part of the processing by the POC computer comprises the function of identifying the initiating of a message part, clearing the buffer ready to receive the message part and sending an acknowledgement. This function can be coded as a definition object of type B. It is instantiated with parameters such as the initiating character <ENQ> and response character of <ACK> and hence it is an object type B instantiation 1.

If the communication is not <ENQ> and is instead a message part framed by <STX> and <ETX> (step S64), in step S65 the POC computer writes the message part to the buffer and in step S66 returns <ACK> and waits for the next message (step S60). This part of the processing by the POC computer comprises the function of identifying a frame of a message block, storing it and sending an acknowledgement. This function can be coded as a definition object of type C. It is instantiated with parameters such as the message frame characters <STX> and <ETX> and response character of <ACK> and hence it is an object type C instantiation 2.

If the communication is <EOT> (step S67), the completed message stored in the buffer is transmitted by the POC computer 30 over the network 10 to the service provider's computer 60 (step S68) and an ACK response is returned to the POC device. The POC computer 30 then waits for the next message (step S60). This function can be coded as a definition object of type D. It is instantiated with parameters such as the character <EOT> and details of the service to which the message is transmitted and the character <ACK> and hence it is an object type D instantiation 1.

If the POC computer detects a message character other than <ENQ>, <STX> or <EOT>, an error message is generated in step S69.

Hence, in this embodiment, the code required by the POC computer 30 to process communications with a POC device 11 is based on the instantiation of the same four definition objects as the embodiment of FIG. 7. However, this embodiment differs in that the processing of the communications with the type B POC device is characterised by a different instantiation of object C: there are no partial message frames framed by <STX> and <ETB> in this embodiment.

Figure 9:
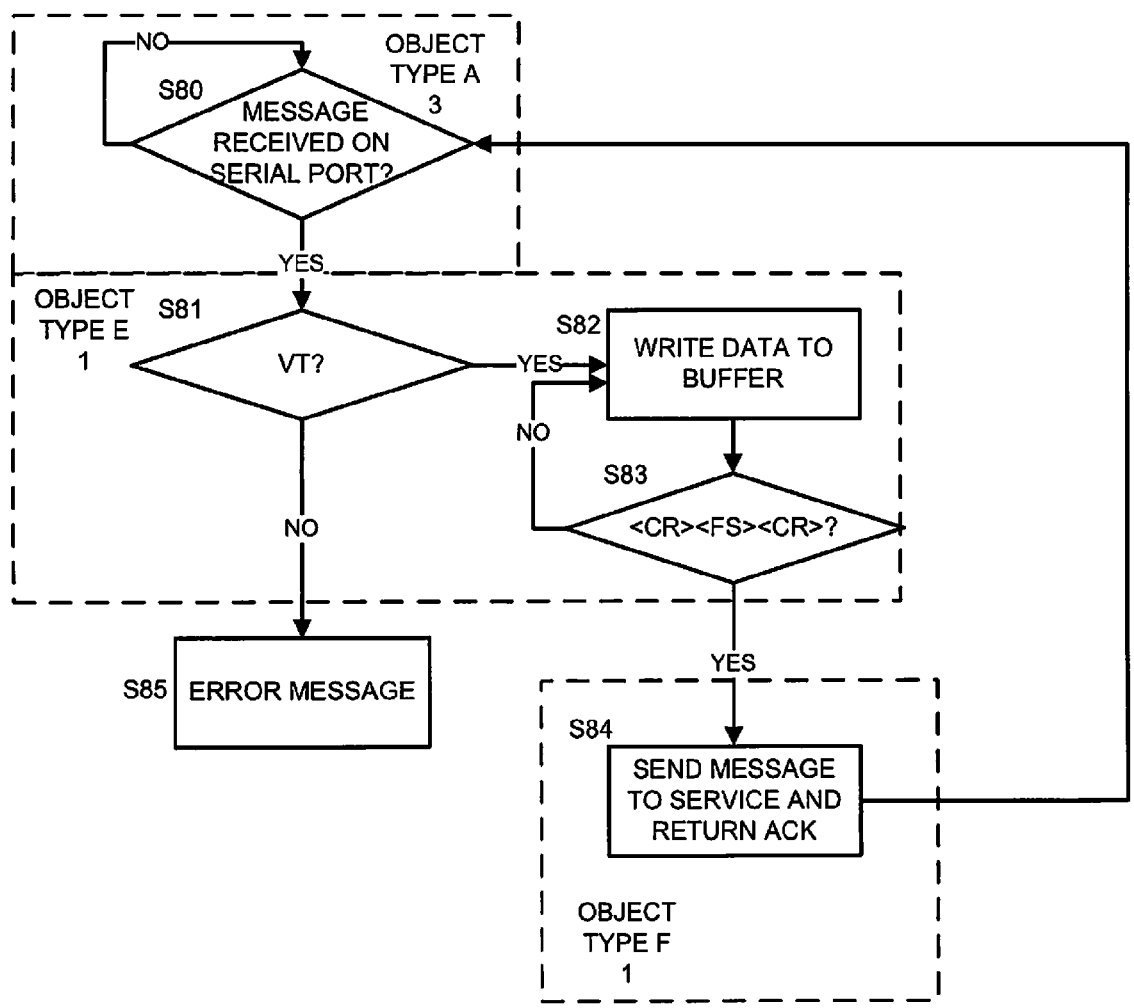
FIG. 9 is a flow diagram illustrating the process for processing patient test data from a point of care device of a third type according to one embodiment.

FIG. 9 illustrates a process implemented by processing code for processing data from a POC device of type C. In this embodiment, the POC device communicates using a different communication protocol. As before, the communication between the POC device and the POC computer is two way. In this embodiment, there is no transmission of an <ACK> character at the end of receipt of each message part to prompt the POC device to send the next.

In step S80 the POC computer waits in a monitoring state to receive a message on a serial port in this embodiment. The function of monitoring a port can be coded as a definition object, e.g. object type A. In this instance the object is instantiated by instantiation data to monitor the serial port and hence it is an object type A instantiation 3. In step S81 the process determines whether the communication is <VT> and if so, the data is received from the POC device 11 and stored in a temporary buffer (step S82) until <CR> <FS<CR> is received from the POC device indicating the end of the message (step S83). This function can be coded as a definition object of type E. It is instantiated with parameters such as the character <VT> and the character sequence <CR> <FS<CR>.

When receipt of the message is complete the data is read from the buffer and transmitted by the POC computer 30 over the network 10 to the service provider's computer 60 (step S84) and an <ACK> is returned to the POC device. The POC computer 30 then waits for the next message (step S80). This function can be coded as a definition object of type F. It is instantiated with parameters such as the details of the service to which the message is transmitted and the character <ACK> and hence it is an object type F instantiation 1.

If the POC computer detects a message character other than <VT>, an error message is generated in step S85.

FIG. 10 is a diagram illustrating the definition objects and the instantiation data stored for the three embodiments described with reference to FIGS. 7 to 9.

For each POC device type, in the service provider's computer 60 in addition to the library of definition objects, instantiation data is stored. The instantiation data comprises instantiation data for each definition object and can include parameters identifying the sequence of objects in the processing of the communications with the POC device. In one embodiment, the type A and B POC devices may transmit a known number of message parts processed by definition objects C and hence the sequence is defined by instantiation parameters. In another embodiment, the number of message parts transmitted by a POC device might vary depending upon the nature of the patient test data e.g. whether a test was run for 1 hour or 2. In such an embodiment, the instantiation parameters for object type C for POC devices type A and B can simply instantiate a conditional clause in the function requiring the code to identify if the message is <STX> or <EOT> and invoke the instantiated definition object accordingly.

Although the previous embodiments have been described with reference to the ASTM protocol, embodiments are applicable to any communication protocol used by POC devices.

Figure 11:
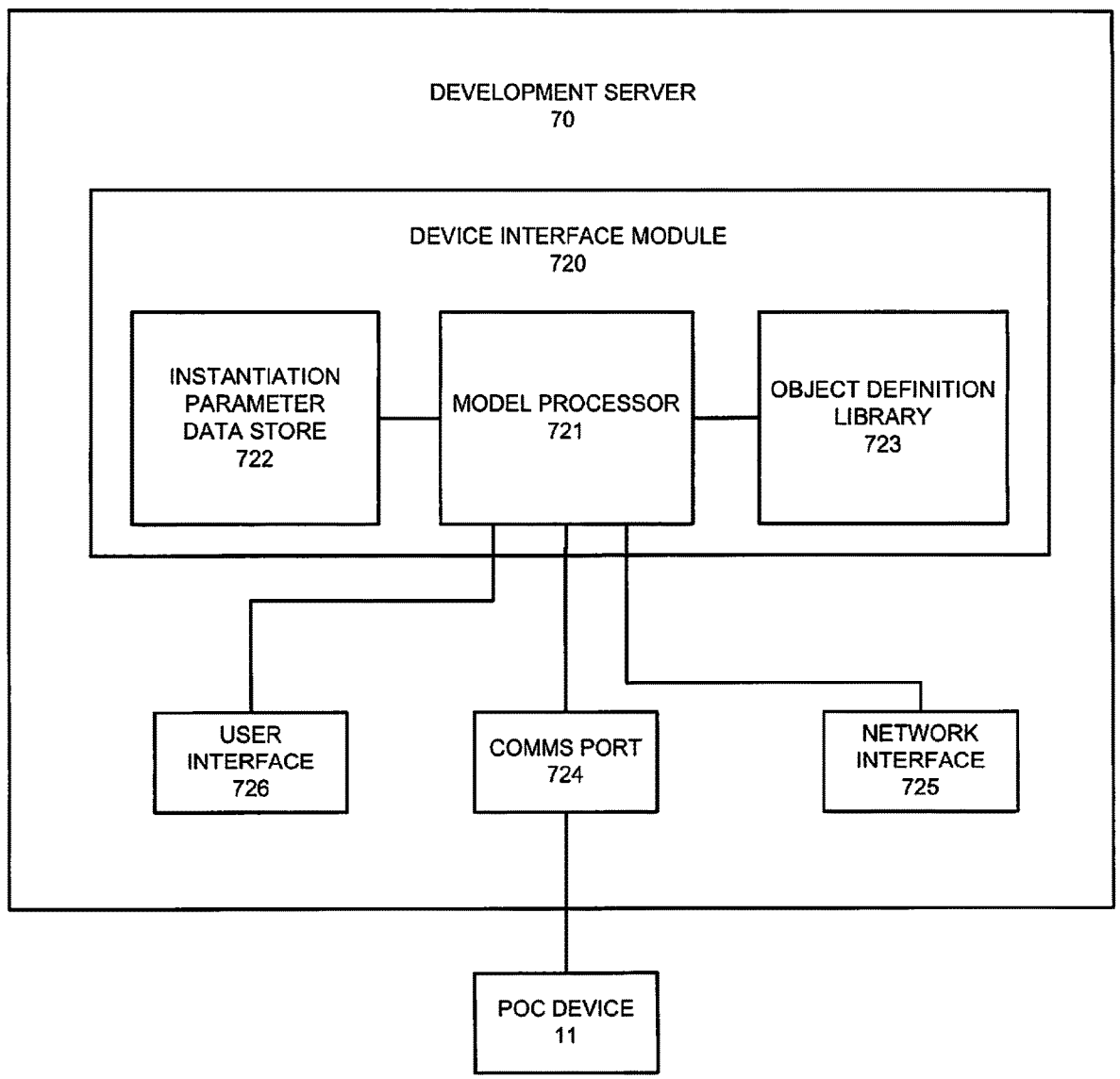
FIG. 11 is a schematic diagram of a development server for developing definition objects and instantiation parameters for generating code for processing patient test data according to one embodiment.

FIG. 11 is a schematic diagram of a development server 70 for use with the system of FIG. 1 in accordance with one embodiment of the invention.

The development server 70 includes a network 725 for connection to a network such as the internet for communication with the service provider's computer 60. The development server 70 includes a device interface module 720 which performs similar functions to the device interface module of FIG. 3. A model processor 721 is provided to access an object definition library 723 and an instantiation parameter data store 722. A communications port 724 is provided to provide communications with a point of care device 11. The processor 721 is operable to enable a user to access the object definition library 723a user interface 726 to be able to select of add objects and to access the instantiation parameter data store 722 to select and change or add instantiation parameters in a development process which is described in more detail with reference to FIGS. 5 and 6.

This embodiment enables a developer to develop the definition objects and instantiation parameters in a development environment away from the service provider's computer 60. The developed definition objects and instantiation parameters can then be uploaded to the service provider's computer 60 from the development server 70 for storage in the definition object library 623 and instantiation parameter data store 622. Any revisions to the definition object library 623 can be transmitted to all POC computers 20 and 30 connected over the network to the service provider's computer 60 for storage in the definition object library 102 so that each POC computer has available all of the object for all know POC devices. The instantiation parameters will be downloaded by the POC computers when needed for the instantiation of the definition objects to generate the code for communication with the POC device.

Figure 12:
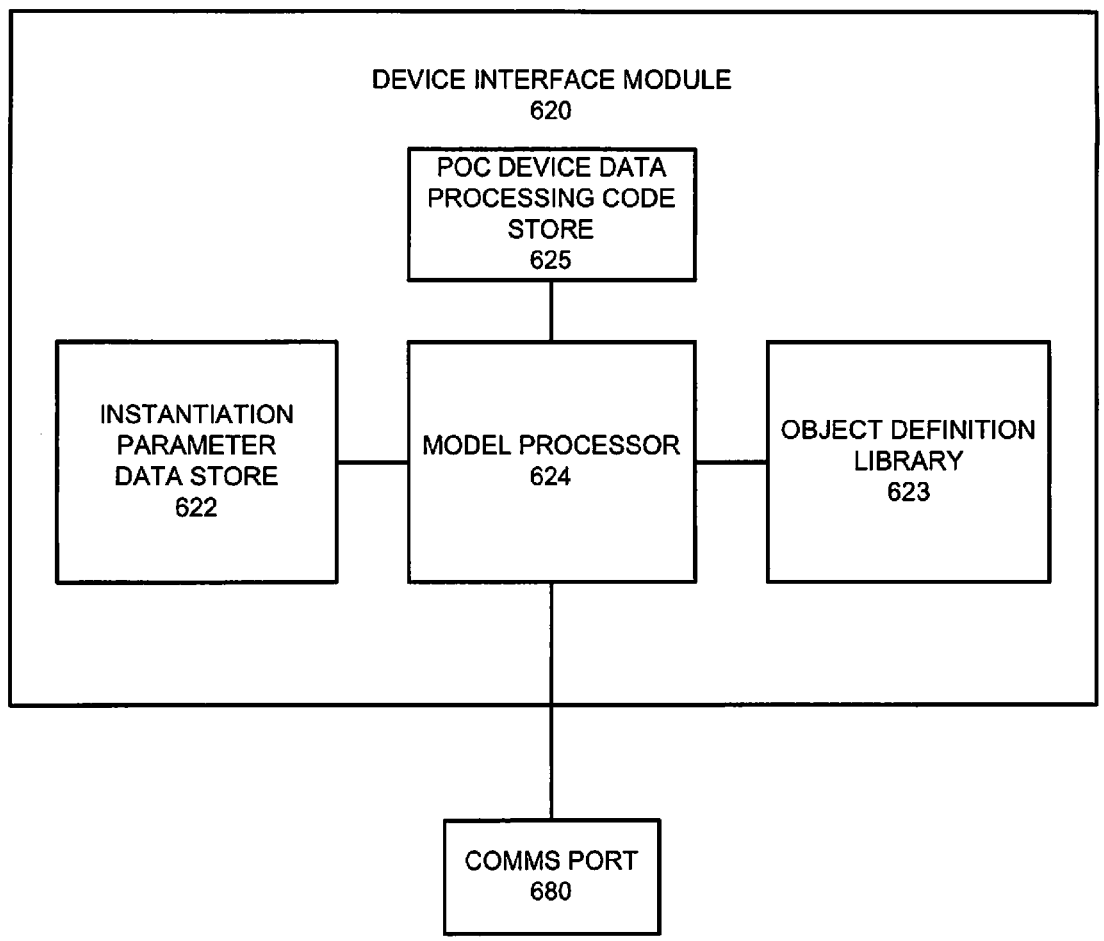
FIG. 12 is a schematic diagram of the details of an alternative device interface module of FIG. 2 according to an alternative embodiment.

FIG. 12 is a schematic diagram of the device interface 620 of FIG. 2 according to another embodiment. This embodiment has similar features and functionality to those of the embodiment of FIG. 3. This embodiment differs in that a POC device data processing code store 625 is provided in which is stored code for execution by the POC computers to communicate with the POC devices. The model processor 624 generates the code using the instantiation parameters for definition objects for POC devices to provide a library of code which can be downloaded to the POC computers for execution when required for new POC devices connected to the POC computers. Hence, this embodiment differs from the embodiment of FIG. 3 in that instead of downloading just instantiation parameters to the POC computers, POC device data processing code is downloaded ready for execution by the POC computer.

Figure 13:
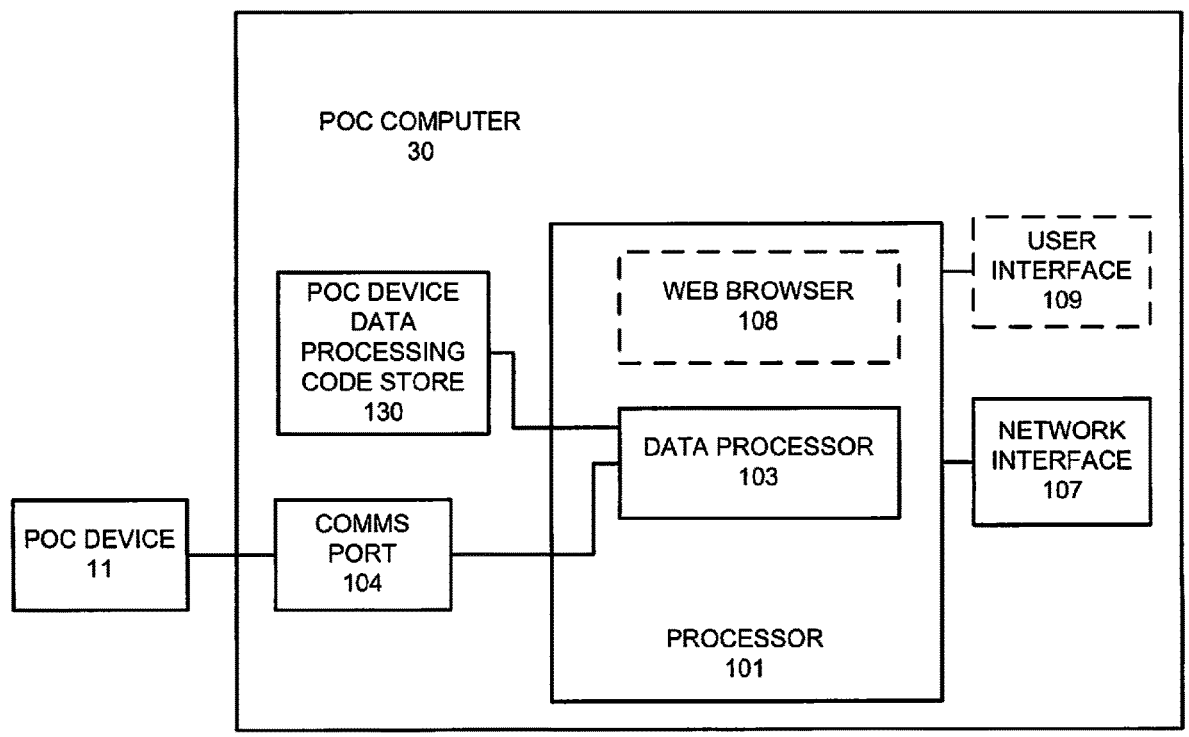
FIG. 13 is a schematic diagram of an alternative point of care (POC) computer according to an alternative embodiment.

FIG. 13 schematically illustrates a POC computer 30 for use with the device interface module 620 of the embodiment of FIG. 12. This embodiment is similar to the embodiment of FIG. 4 except that there is no instantiation data store, instantiation engine, definition object library or generated code store. Instead, the data processor 103 simply accesses a POC device data processing code store 130 to access and execute the required code for communication with the POC device.

Figure 14:
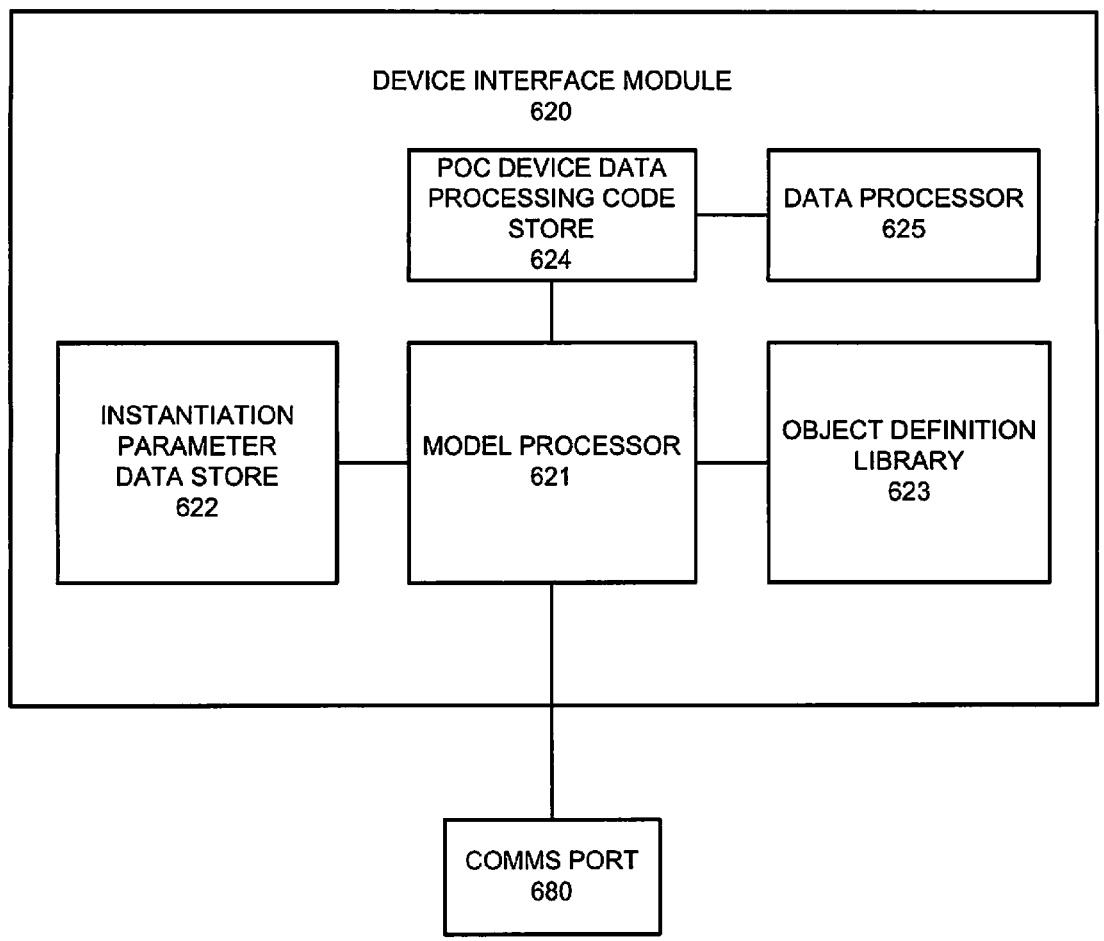
FIG. 14 is a schematic diagram of the details of another alternative device interface module of FIG. 2 according to another embodiment.

FIG. 14 schematically illustrates a device interface module 620 according to another embodiment. This embodiment is similar to the embodiment of FIG. 12 except that there is additionally provided a data processor 625 for executing the POC device data processing code in the code store 624.

Figure 15:
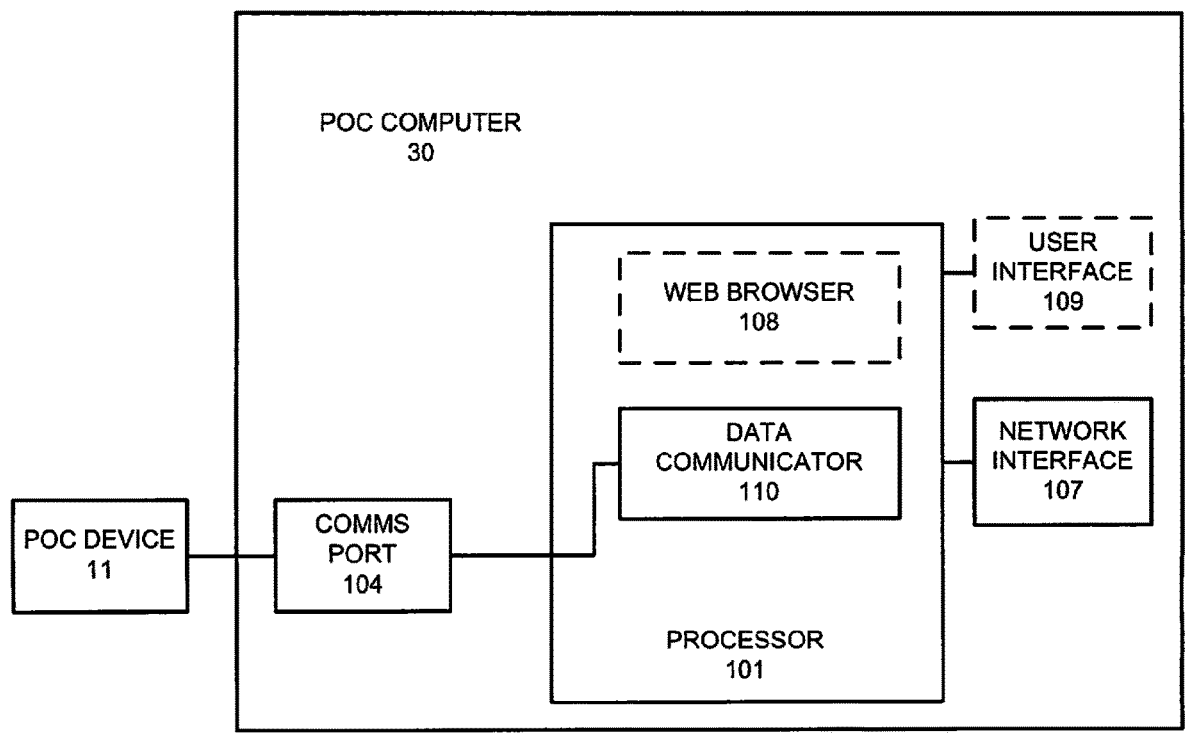
FIG. 15 is a schematic diagram of another alternative point of care (POC) computer according to another embodiment.

FIG. 15 is a schematic diagram of a POC computer for use with the embodiment of FIG. 14. This embodiment differs from the embodiment of FIG. 13 in that the processor does not implement a data processor using code in a POC device data processing code store. Instead a data communicator 110 is implemented by the processor 101 to simply act to pass on communications received from the POC device to the service provider's computer 60. The processing of the communications is performed in the device interface module 620 by the data processor 625. Hence, in this embodiment, the POC computer 30 acts as a 'thin client' and acts as nothing more than a router of communications to the server for processing. In this embodiment the server is providing the POC computer function. This avoids the need for the transmission and copying of code or instantiation parameters to the POC computer. However, the network needs to be fast to avoid transmission delays which can cause the POC device to time out during a communication if the handshaking is not quick enough.

In the embodiments described, the system and method is able to manage the development of new POC device processing code by developing, maintaining and utilising a library of definition objects which can be used for processing a plurality of POC device communications. Each definition object comprising generic code for defining or performing a function, which can comprise part of a complete communication with a POC device. Instantiation parameters can be developed and stored separately to instantiate the definition objects for use in the generation of POC device data processing code. This provides a more flexible code development and deployment system.

It will be readily understood to those skilled in the art that various other changes in the details, material, and arrangements of the parts and method stages which have been described and illustrated in order to explain the nature of the inventive subject matter may be made without departing from the principles and scope of the inventive subject matter as expressed in the subjoined claims.

The invention claimed is:

1. A computer system to process patient test data received from a point of care device, the computer system comprising:
 object storage storing a plurality of objects for a plurality of point of care devices, each object representing a generic function to be performed on an output of a point of care device in response to reception of the output of the point of care device;
 a network interface for receiving instantiation data from a remote computer to instantiate a plurality of objects as a plurality of processing objects, each processing object being for a specific function to be performed in response to the patient test data received from the point of care device when processed with definition objects, wherein the instantiation data includes data identifying said objects for said point of care device and any order of implementation of said objects for the ordered processing of the patient test data, wherein the network interface is configured to receive revisions to the objects from the remote computer; and
 a program code generating processor programmed to generate processor executable program code for a plurality of processing objects to perform a respective plurality of specific processing functions when the generated processor executable program code is run by a data processor to process the patient test data received from the point of care device, the program code generating processor being programmed to generate the processor executable program code, by using the received instantiation data for the point of care device and a plurality of objects in the object storage identified in the instantiation data, to instantiate the plurality of objects using instantiation data for the point of care device as the plurality of processing objects;
 a communications interface for receiving the patient test data from the point of care device; and
 a data processor for processing the received patient test data from the point of care device using the generated code.

2. A computer system according to claim 1, wherein the instantiation data includes parameters related to the data expected to be output from the point of care device and received by the processing objects in the course of the output of a set of point of care data for a patient test, and the data expected to be received by the point of care device from each processing objects in the course of the output of the set of point of care data for the patient test.

3. A method of processing patient test data received from a point of care device, the method comprising:
 storing a plurality of objects for a plurality of point of care devices, each object representing a generic function to be performed on an output of a point of care device in response to reception of the output of the point of care device;
 receiving instantiation data from a remote computer to instantiate a plurality of objects as a plurality of processing objects, each processing object being for a specific function to be performed in response to the patient test data received from the point of care device when processed with definition objects, wherein the instantiation data includes data identifying said objects for said point of care device and any order of implementation of said objects for the ordered processing of the patient test data;
 receiving revisions to the objects from the remote computer;
 generating processor executable program code for a plurality of processing objects to perform a respective plurality of specific processing functions when the generated processor executable program code is run by a data processor to process the patient test data received from the point of care device, wherein the processor executable program code is generated by using the received instantiation data for the point of care device and a plurality of stored objects identified in the instantiation data, to instantiate the plurality of objects using instantiation data for the point of care device as the plurality of processing objects;
 receiving the patient test data from the point of care device; and
 processing the received patient test data from the point of care device using the generated code.

4. The method of claim 3, wherein the instantiation data includes parameters related to the data expected to be output from the point of care device and received by the processing objects in the course of the output of a set of point of care data for a patient test, and the data expected to be received by the point of care device from each processing object in the course of the output of the set of point of care data for the patient test.

5. A non-transient storage medium storing computer readable code for controlling a computer to:

store a plurality of objects for a plurality of point of care devices, each object representing a generic function to be performed on an output of a point of care device in response to reception of the output of the point of care device;

receive instantiation data from a remote computer to instantiate a plurality of objects as a plurality of processing objects, each processing object being for a specific function to be performed in response to the patient test data received from the point of care device when processed with definition objects, wherein the instantiation data includes data identifying said objects for said point of care device and any order of implementation of said objects for the ordered processing of the patient test data;

receive revisions to the objects from the remote computer;

generate processor executable program code for a plurality of processing objects to perform a respective plurality of specific processing functions when the generated processor executable program code is run by a data processor to process the patient test data received from the point of care device, wherein the processor executable program code is generated by using the received instantiation data for the point of care device and a plurality of stored objects identified in the instantiation data, to instantiate the plurality of objects using instantiation data for the point of care device as the plurality of processing objects;

receive the patient test data from the point of care device; and process the received patient test data from the point of care device using the generated code.

6. The non-transient storage medium of claim 5, wherein the instantiation data includes parameters related to the data expected to be output from the point of care device and received by the processing objects in the course of the output of a set of point of care data for a patient test, and the data expected to be received by the point of care device from each processing object in the course of the output of the set of point of care data for the patient test.

* * * * *